(12) United States Patent
Boyle et al.

(10) Patent No.: US 8,992,597 B2
(45) Date of Patent: *Mar. 31, 2015

(54) ENDOLUMINAL CARDIAC AND VENOUS VALVE PROSTHESES AND METHODS OF MANUFACTURE AND DELIVERY THEREOF

(75) Inventors: Christopher T. Boyle, Flushing, NY (US); Steven R. Bailey, San Antonio, TX (US)

(73) Assignee: ABPS Venture One, Ltd., Dallas, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 13/546,384

(22) Filed: Jul. 11, 2012

(65) Prior Publication Data
US 2013/0018449 A1  Jan. 17, 2013

Related U.S. Application Data

(60) Continuation of application No. 12/026,509, filed on Feb. 5, 2008, now Pat. No. 8,221,493, which is a division of application No. 10/260,205, filed on Sep. 30, 2002, now Pat. No. 7,338,520, and a division of application No. 09/477,120, filed on Dec. 31, 1999, now Pat. No. 6,458,153.

(51) Int. Cl.
*A61F 2/06* (2013.01)
*A61F 2/24* (2006.01)

(52) U.S. Cl.
CPC ............ *A61F 2/2418* (2013.01); *A61F 2/2475* (2013.01); *A61F 2220/0008* (2013.01); *A61F 2220/0016* (2013.01); *A61F 2230/005* (2013.01); *A61F 2230/0054* (2013.01); *A61F 2230/0078* (2013.01)

USPC ........................................ 623/1.24; 623/2.18

(58) Field of Classification Search
USPC ................... 623/1.24, 1.26, 2.11, 2.14, 2.18
See application file for complete search history.

(56) References Cited

U.S. PATENT DOCUMENTS

| | | | |
|---|---|---|---|
| 3,197,788 A | 8/1965 | Segger | 3/1 |
| 3,874,388 A | 4/1975 | King et al. | 128/334 R |
| 4,222,126 A * | 9/1980 | Boretos et al. | 623/2.19 |
| 4,655,771 A | 4/1987 | Wallsten | 623/1 |
| 4,994,077 A | 2/1991 | Dobben | 623/2 |
| 5,007,926 A | 4/1991 | Derbyshire | 623/1 |

(Continued)

FOREIGN PATENT DOCUMENTS

| | | | | |
|---|---|---|---|---|
| EP | 0808614 | 11/1997 | | A61F 2/06 |
| EP | 0850607 | 7/1998 | | A61F 2/24 |

(Continued)

OTHER PUBLICATIONS

"Aortic Valve Replacement", STS Patient Information, Society of Thoracic Surgeons, pp. 1-5, (Dec. 2, 1999), http://www.sts.org/doc/3620 (Dec. 7, 1999).

"ATS Medical Inc. (ATSI) Annual Report (SEC Form 10-K): Management's Discussion and Analysis of Financial Condition and Results of Operations", ATSI Medical Inc., pp. 1-7, (Mar. 30, 1999), http://biz.yahoo.com/e/990330/atsi.html (Dec. 7, 1999).

(Continued)

*Primary Examiner* — Alvin Stewart
(74) *Attorney, Agent, or Firm* — David G. Rosenbaum; J. Peter Paredes; Rosenbaum IP, P.C.

(57) ABSTRACT

This invention relates to prosthetic cardiac and venous valves and a single catheter device and minimally invasive techniques for percutaneous and transluminal valvuloplasty and prosthetic valve implantation.

13 Claims, 6 Drawing Sheets

(56) References Cited

U.S. PATENT DOCUMENTS

| | | | |
|---|---|---|---|
| 5,078,720 A | 1/1992 | Burton et al. | 606/108 |
| 5,108,420 A | 4/1992 | Marks | 606/213 |
| 5,163,953 A | 11/1992 | Vince | 623/2 |
| 5,332,402 A | 7/1994 | Teitelbaum | 623/2 |
| 5,334,217 A | 8/1994 | Das | 606/216 |
| 5,370,685 A | 12/1994 | Stevens | 623/2 |
| 5,397,351 A | 3/1995 | Pavcnik et al. | 623/11 |
| 5,411,552 A | 5/1995 | Andersen et al. | 623/2 |
| 5,476,506 A | 12/1995 | Lunn | 623/1 |
| 5,500,014 A * | 3/1996 | Quijano et al. | 623/1.24 |
| 5,545,214 A | 8/1996 | Stevens | 623/2 |
| 5,562,728 A | 10/1996 | Lazarus et al. | 623/1 |
| 5,607,444 A | 3/1997 | Lam | 606/194 |
| 5,639,274 A | 6/1997 | Fischell et al. | 604/96 |
| 5,662,703 A | 9/1997 | Yurek et al. | 623/1 |
| 5,713,953 A * | 2/1998 | Vallana et al. | 623/2.15 |
| 5,725,552 A | 3/1998 | Kotula et al. | 606/213 |
| 5,741,297 A | 4/1998 | Simon | 606/213 |
| 5,824,063 A | 10/1998 | Cox | 623/2 |
| 5,824,064 A | 10/1998 | Taheri | 623/2 |
| 5,840,081 A | 11/1998 | Andersen et al. | 623/2 |
| 5,843,090 A | 12/1998 | Schuetz | 606/108 |
| 5,846,261 A | 12/1998 | Kotula et al. | 606/213 |
| 5,855,597 A | 1/1999 | Jayaraman | 623/1 |
| 5,855,601 A | 1/1999 | Bessler et al. | 623/2 |
| 5,861,003 A | 1/1999 | Latson et al. | 606/213 |
| 5,895,419 A | 4/1999 | Tweden et al. | 623/2 |
| 5,919,224 A | 7/1999 | Thompson et al. | 623/1 |
| 5,925,063 A | 7/1999 | Khosravi | 606/200 |
| 5,954,766 A | 9/1999 | Zadno-Azizi et al. | 623/2 |
| 5,957,949 A * | 9/1999 | Leonhardt et al. | 623/1.1 |
| 5,964,782 A | 10/1999 | Lafontaine et al. | 606/213 |
| 5,993,485 A | 11/1999 | Beckers | 623/12 |
| 5,997,573 A | 12/1999 | Quijano et al. | 623/1 |
| 6,027,525 A * | 2/2000 | Suh et al. | 623/1.1 |
| 6,120,534 A | 9/2000 | Ruiz | 623/1.19 |
| 6,124,523 A | 9/2000 | Banas et al. | 623/11 |
| 6,168,614 B1 | 1/2001 | Andersen et al. | 623/1 |
| 6,168,621 B1 | 1/2001 | Vrba | 623/1.2 |
| 6,231,588 B1 | 5/2001 | Zadno-Azizi | 606/200 |
| 6,241,757 B1 * | 6/2001 | An et al. | 623/1.1 |
| 6,254,564 B1 | 7/2001 | Wilk et al. | 604/9 |
| 6,254,633 B1 | 7/2001 | Pinchuk et al. | 623/1.3 |
| 6,287,339 B1 | 9/2001 | Vazquez et al. | 623/2.4 |
| 6,299,637 B1 | 10/2001 | Shaolian et al. | 623/1.24 |
| 6,338,740 B1 | 1/2002 | Carpentier | 623/2.13 |
| 6,419,695 B1 | 7/2002 | Gabbay | 623/2.36 |
| 6,425,916 B1 * | 7/2002 | Garrison et al. | 623/2.11 |
| 6,440,164 B1 * | 8/2002 | DiMatteo et al. | 623/1.24 |
| 6,454,799 B1 * | 9/2002 | Schreck | 623/2.18 |
| 6,458,153 B1 | 10/2002 | Bailey et al. | 623/1.24 |
| 6,485,496 B1 | 11/2002 | Suyker et al. | 606/153 |
| 6,511,491 B2 | 1/2003 | Grudem et al. | 606/153 |
| 6,527,800 B1 | 3/2003 | McGuckin, Jr. et al. | 623/1.24 |
| 6,558,429 B2 * | 5/2003 | Taylor | 623/23.68 |
| 6,579,314 B1 | 6/2003 | Lombardi et al. | 623/1.44 |
| 6,599,303 B1 | 7/2003 | Peterson et al. | 606/153 |
| 6,616,675 B1 | 9/2003 | Evard et al. | 606/155 |
| 6,652,578 B2 * | 11/2003 | Bailey et al. | 623/1.24 |
| 6,669,724 B2 * | 12/2003 | Park et al. | 623/1.24 |
| 6,676,698 B2 | 1/2004 | McGuckin, Jr. et al. | 623/1.14 |
| 6,676,699 B2 * | 1/2004 | Shiu | 623/1.24 |
| 6,695,878 B2 | 2/2004 | McGuckin, Jr. et al. | 623/1.19 |
| 6,730,118 B2 | 5/2004 | Spenser et al. | 623/1.24 |
| 6,790,229 B1 | 9/2004 | Berreklouw | 623/2.1 |
| 6,790,230 B2 | 9/2004 | Beyersdorf et al. | 623/2.18 |
| 6,840,957 B2 * | 1/2005 | DiMatteo et al. | 623/1.24 |
| 6,893,460 B2 | 5/2005 | Spenser et al. | 623/2.14 |
| 6,908,481 B2 * | 6/2005 | Cribier | 623/2.11 |
| 6,951,571 B1 | 10/2005 | Srivastava | 623/1.24 |
| 6,953,476 B1 | 10/2005 | Shalev | 623/1.15 |
| 6,974,474 B2 | 12/2005 | Pavcnik et al. | 623/1.24 |
| 7,018,406 B2 * | 3/2006 | Seguin et al. | 623/2.1 |
| 7,018,408 B2 | 3/2006 | Bailey et al. | 623/2.11 |
| 7,025,780 B2 * | 4/2006 | Gabbay | 623/2.13 |
| 7,041,128 B2 | 5/2006 | McGuckin, Jr. et al. | 623/1.36 |
| 7,175,656 B2 | 2/2007 | Khairkhahan | 623/1.26 |
| 7,195,641 B2 * | 3/2007 | Palmaz et al. | 623/2.18 |
| 7,201,772 B2 | 4/2007 | Schwammenthal et al. | 623/2.18 |
| 7,338,520 B2 * | 3/2008 | Bailey et al. | 623/1.24 |
| 7,351,256 B2 * | 4/2008 | Hojeibane et al. | 623/1.24 |
| 7,377,938 B2 | 5/2008 | Sarac et al. | 623/1.26 |
| 7,381,219 B2 | 6/2008 | Salahieh et al. | 623/2.11 |
| 7,381,220 B2 | 6/2008 | Macoviak et al. | 623/2.12 |
| 7,393,360 B2 | 7/2008 | Spenser et al. | 623/2.18 |
| 7,399,315 B2 | 7/2008 | Lobbi | 623/1.26 |
| 7,442,204 B2 | 10/2008 | Schwammenthal et al. | 623/1.24 |
| 7,455,677 B2 | 11/2008 | Vargas et al. | 606/153 |
| 7,575,586 B2 | 8/2009 | Berg et al. | 606/215 |
| 7,611,535 B2 | 11/2009 | Woolfson et al. | 623/2.38 |
| 7,799,069 B2 * | 9/2010 | Bailey et al. | 623/1.26 |
| 2001/0002443 A1 | 5/2001 | Parodi | 623/1.13 |
| 2001/0044647 A1 | 11/2001 | Pinchuk et al. | 623/1.13 |
| 2002/0165606 A1 | 11/2002 | Wolf et al. | 623/1.24 |
| 2003/0014104 A1 | 1/2003 | Cribier | 623/2.11 |
| 2003/0023300 A1 * | 1/2003 | Bailey et al. | 623/1.13 |
| 2003/0040792 A1 | 2/2003 | Gabbay | 623/2.11 |
| 2005/0080444 A1 | 4/2005 | Kraemer et al. | 606/192 |
| 2005/0137695 A1 | 6/2005 | Salahieh et al. | 623/2.11 |
| 2005/0165344 A1 | 7/2005 | Dobak, III | 604/8 |
| 2005/0267567 A1 | 12/2005 | Shalev | 623/1.31 |
| 2005/0288786 A1 | 12/2005 | Chanduszko | 623/11.11 |
| 2006/0167543 A1 * | 7/2006 | Bailey et al. | 623/2.18 |
| 2006/0265054 A1 | 11/2006 | Greenhalgh et al. | 623/1.31 |
| 2009/0240320 A1 | 9/2009 | Tuval et al. | 623/1.24 |

FOREIGN PATENT DOCUMENTS

| | | | |
|---|---|---|---|
| JP | 60228366 | 11/1985 | B66B 1/18 |
| JP | 61-076153 | 4/1986 | A61F 2/24 |
| JP | 63-111874 | 5/1988 | A61L 27/00 |
| JP | 05-269192 | 10/1993 | A61L 27/00 |
| WO | 99/38544 | 8/1999 | A61L 27/00 |
| WO | 00/18333 | 4/2000 | A61F 2/24 |
| WO | WO00/47139 | 8/2000 | A61F 2/24 |
| WO | WO01/28459 | 4/2001 | A61F 2/24 |

OTHER PUBLICATIONS

Corcoran, et al., "The Valve of Vieussens: An Important Cause of Difficulty in Advancing Catheters into the Cardiac Veins", *Journal of Cardiovascular Electrophysiology* 10(6): 804-808, (1999), Abstract Only http://www.ncbi.nlm.nih.gov/entrez/guery.fcgi?cmd=retrieve&db=pubmed&list_uids=1037 (Mar. 6, 2003).

DM Cosgrove, "Minimally Invasive Aortic Valve Surgery", CTSNET Experts' Techniques, Adult Cardiac Surgical Techniques, pp. 1-4, http://www.ctsnet.org.org/doc.3358 (Dec. 7, 1999).

Heartport Inc., "Heartport Announces Launch of Heartport inSite AVR System for Less Invasive Aortic Valve Replacement", Heartport, Inc. What's New Release, pp. 1-2, (Oct. 8, 1999), www.pddnet.com/pddnews/08oct.9903.htm (Dec. 7, 1999).

Hynes, et al., "Predictive Valve of Pulmonary Venous Flow Patterns in Detecting Mitral Regurgitation and Left Ventricular Abnormalities", *Canadian Journal of Cardiology* 15(6): 665-670, (1999), Abstract Only http://www.ncbi.nlm.nih.gov/entrez/query.fcgi?cmd=retrieve&db=pubmed&list_uids=1037 (Mar. 6, 2003).

Kin, et al., "A Case of Constrictive Pericarditis with Atrial Fibrillation After Mitral Valve Repair and Maze III Procedure", *Japanese Journal of Thoracic Cardiovascular Surgery* 46(12): 1363-1367, (1998), Abstract Only http://www.ncbi.nlm.nih.gov/entrez/query.fcgi?cmd=retrieve&db=pubmed&list_uids=1037 (Mar. 6, 2003).

Mid Atlantic Medical Associates, "MASA Heart Valves", http://www.heart-surgeons.com/valvedesign.htm, pp. 1-3, (Dec. 7, 1999).

St. Jude Medical Inc., "St. Jude Medical Heart Valve Division—Expanding the Focus", www.sum.com/stjde/world.htm/expand.htm (Dec. 7, 1999).

St. Jude Medical Inc., "St. Jude Medical Heart Valve Division—The Mechanical Heart Valve Evolution", www.sjm.com/stjude/world/htm.evolut.htm (Dec. 7, 1999).

\* cited by examiner

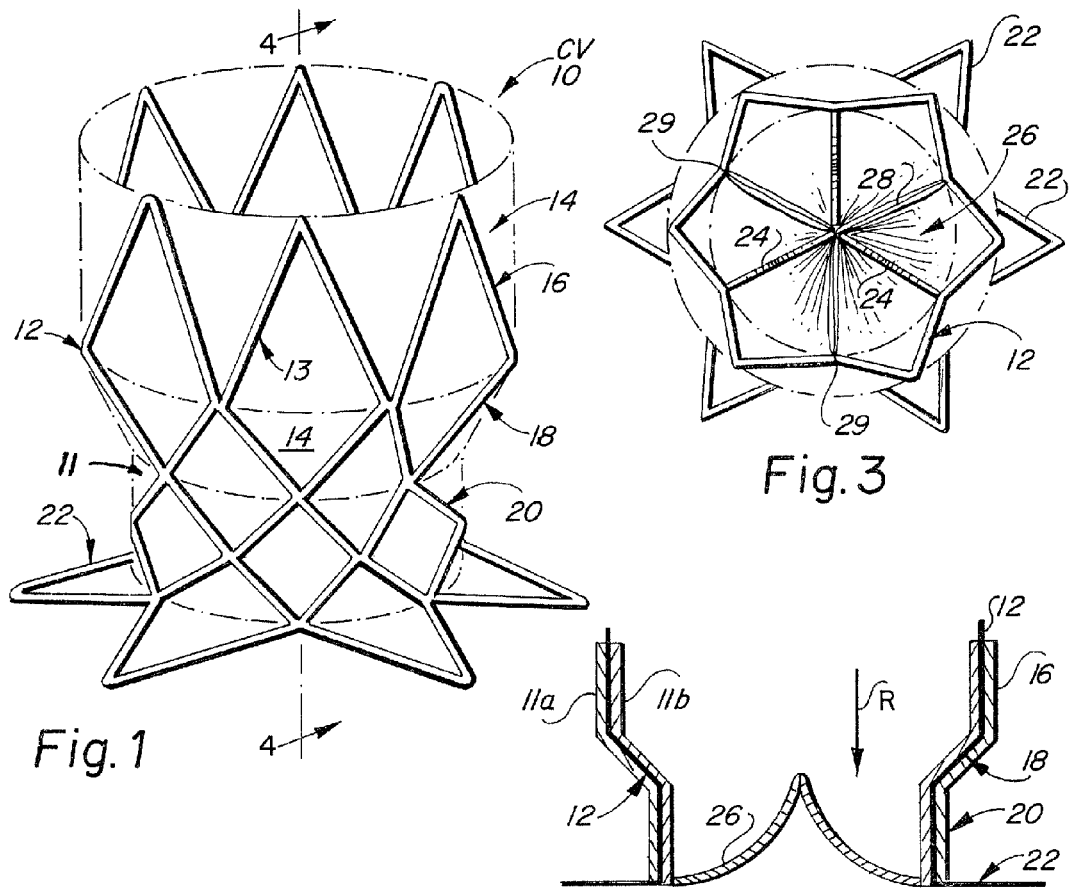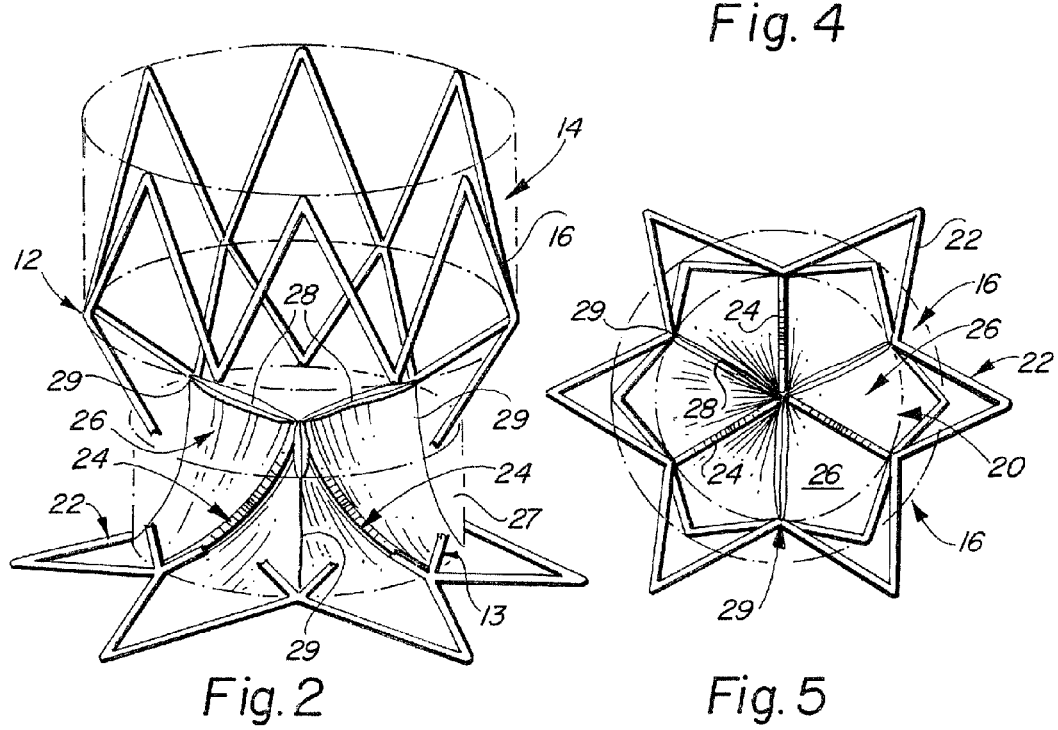

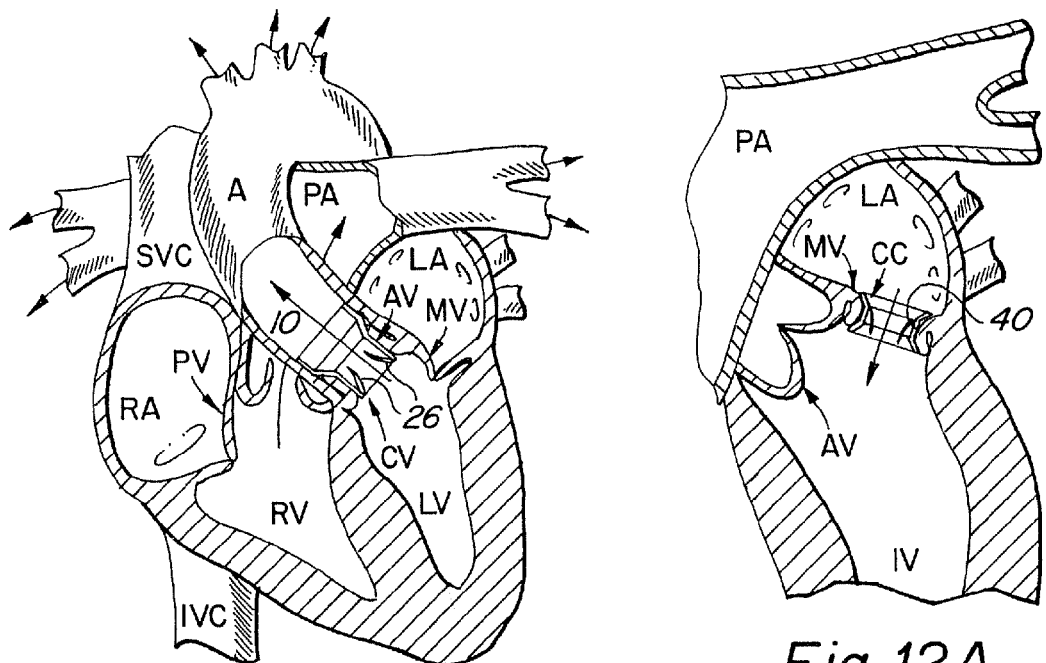
Fig. 6A
Fig. 12A
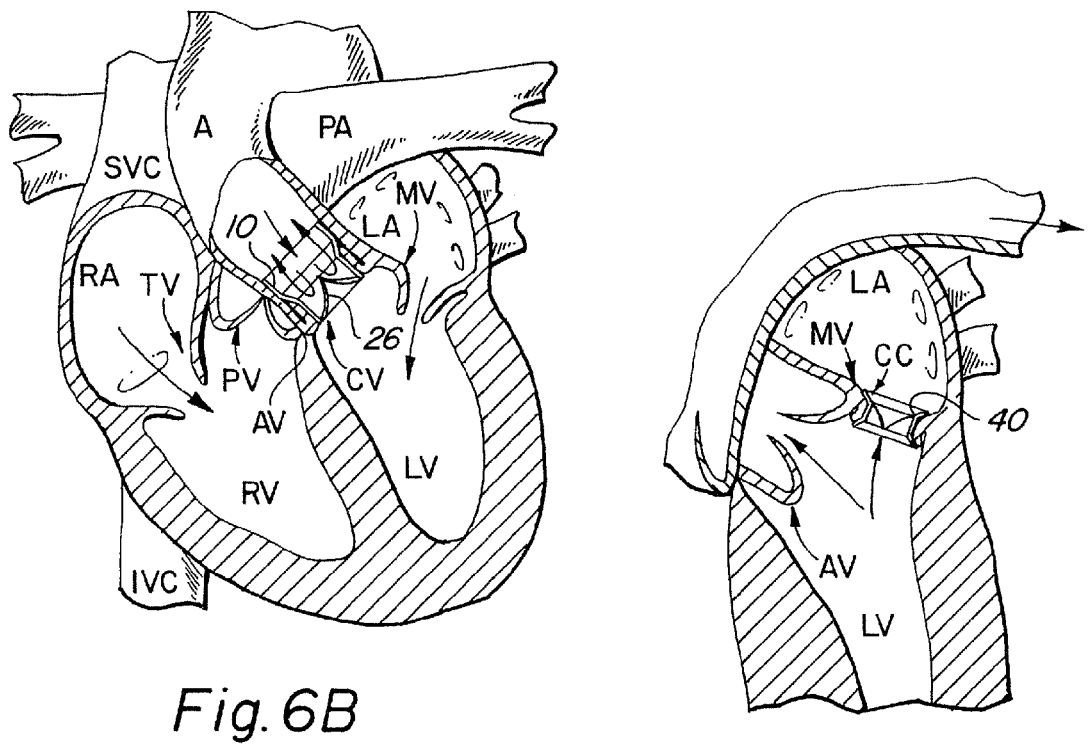
Fig. 6B
Fig. 12B

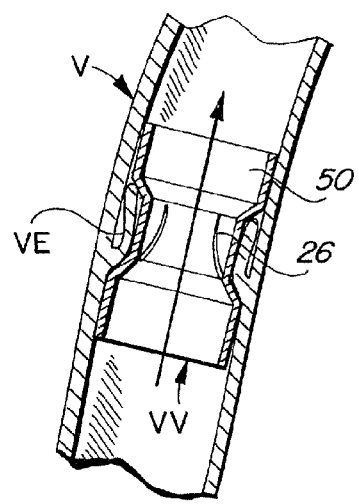
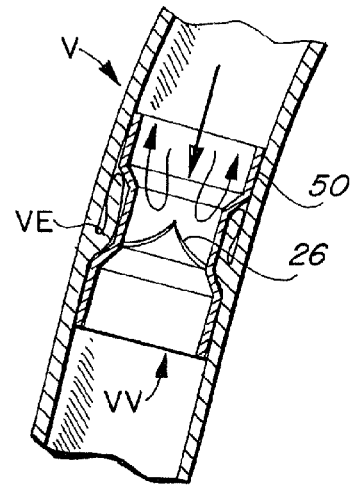
Fig. 18A    Fig. 18B
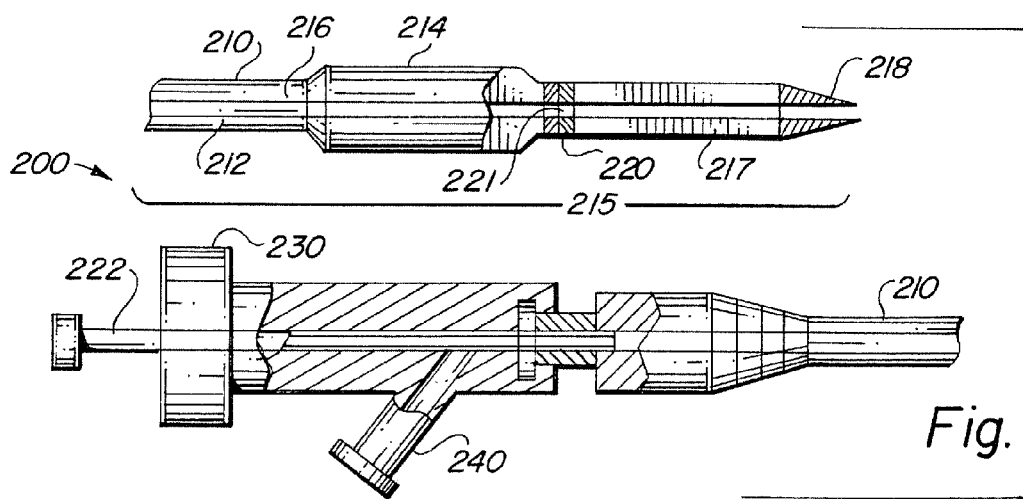
Fig. 19
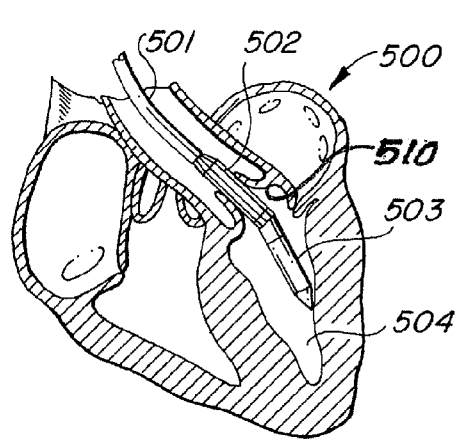
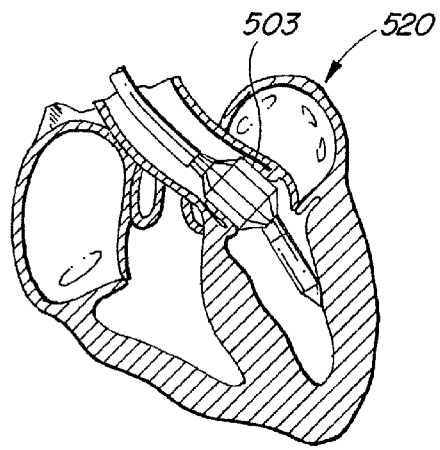
Fig. 20A    Fig. 20B

ENDOLUMINAL CARDIAC AND VENOUS VALVE PROSTHESES AND METHODS OF MANUFACTURE AND DELIVERY THEREOF

CROSS-REFERENCE TO RELATED APPLICATIONS

This application is a continuation of U.S. patent application Ser. No. 12/026,509, filed Feb. 5, 2008, which is a divisional of U.S. patent application Ser. No. 10/260,205, filed Sep. 30, 2002, now U.S. Pat. No. 7,338,520, issued Mar. 4, 2008, which is a divisional of U.S. patent application Ser. No. 09/477,120, filed Dec. 31, 1999, now U.S. Pat. No. 6,458,153, issued Oct. 1, 2002, each incorporated by reference in their entirety.

BACKGROUND OF THE INVENTION

The present invention relates generally to implantable prosthetic cardiac and venous valves. More particularly, the present invention pertains to prosthetic cardiac and venous valve implants which are capable of being delivered using endovascular techniques and being implanted at an intracardiac or intravenous site without the need for anatomic valve removal.

The prior art discloses certain common device segments inherently required by a percutaneous prosthetic valve: an expandable stent segment, an anchoring segment and a flow-regulation segment. Prior art percutaneous prosthetic valve devices include the Dobben valve, U.S. Pat. No. 4,994,077, the Vince valve, U.S. Pat. No. 5,163,953, the Teitelbaum valve, U.S. Pat. No. 5,332,402, the Stevens valve, U.S. Pat. No. 5,370,685, the Pavcnik valve, U.S. Pat. No. 5,397,351, the Taheri valve, U.S. Pat. No. 5,824,064, the Anderson valves, U.S. Pat. Nos. 5,411,552 & 5,840,081, the Jayaraman valve, U.S. Pat. No. 5,855,597, the Besseler valve, U.S. Pat. No. 5,855,601, the Khosravi valve, U.S. Pat. No. 5,925,063, the Zadano-Azizi valve, U.S. Pat. No. 5,954,766, and the Leonhardt valve, U.S. Pat. No. 5,957,949. Each of these pre-existing stent valve designs has certain disadvantages which are resolved by the present invention.

The Dobben valve has a disk shaped flap threaded on a wire bent like a safety pin to engage the vessel wall and anchor the valve. A second embodiment uses a stent of a cylindrical or crown shape that is made by bending wire into a zigzag shape to anchor the device and attach the flow regulator flap. The device presents significant hemodynamic, delivery, fatigue and stability disadvantages.

The Vince valve has a stent comprised of a toroidal body formed of a flexible coil of wire and a flow-regulation mechanism consisting of a flap of biologic material. Numerous longitudinal extensions within the stent are provided as attachment posts to mount the flow-regulation mechanism. The device requires balloon expansion to deliver to the body orifice. The main shortcoming of this design is delivery profile. Specifically, the device and method put forth will require a 20+ French size catheter (approximately 9 French sizes to accommodate the balloon and 14+ French sizes to accommodate the compressed device) making the device clinically ineffective as a minimally invasive technique. Additionally, the device does not adequately address hemodynamic, stability and anchoring concerns.

The Teitelbaum valve is made of shape memory nitinol and consists of two components. The first component is stent-like and comprised of a meshwork or braiding of nitinol wire similar to that described by Wallsten, U.S. Pat. No. 4,655,771, with trumpet like distal a proximal flares. The purpose of the stent is to maintain a semi-ridged patent channel through the diseased cardiac valve after initial balloon dilation. The flared ends are intended to maintain the position of the stent component across the valve thereby anchoring the device. Embodiments for the flow-regulation mechanism include a sliding obturator and a caged ball both which are delivered secondary to the stent portion. The disadvantages of the device are the flow regulators reduce the effective valve orifice and generate sub-optimal hemodynamic characteristics; fatigue concerns arise from the separate nature of the stent and flow-regulation components; the high metal and exposed metal content raises thrombogenesis, valvular stenosis and chronic anticoagulation concerns; and the separate delivery requirements (although addressing the need for small delivery profile) in addition to any initial valvuloplasty performed increases the time, costs, risks, difficulty and trauma associated with the percutaneous procedure.

The Pavcnik valve is a self-expanding percutaneous device comprised of a poppet, a stent and a restraining element. The valve stent has barbed means to anchor to the internal passageway. The device includes a self-expanding stent of a zigzag configuration in conjunction with a cage mechanism comprised of a multiplicity of crisscrossed wires and a valve seat. The disadvantages of the device include large delivery profile, reduced effective valvular orifice, possible perivalvular leakage, trauma-inducing turbulent flow generated by the cage occlusive apparatus and valve seat, thrombogenesis, valvular stenosis, chronic anticoagulation, problematic physiological and procedural concerns due to the barb anchors and complex delivery procedure that includes inflation of occlusive member after initial implantation.

Stevens discloses a percutaneous valve replacement system for the endovascular removal of a malfunctioning valve followed by replacement with a prosthetic valve. The valve replacement system may include a prosthetic valve device comprised of a stent and cusps for flow-regulation such as a fixed porcine aortic valve, a valve introducer, an intraluminal procedure device, a procedure device capsule and a tissue cutter. The devices disclosed indicate a long and complex procedure requiring large diameter catheters. The valve device disclosed will require a large delivery catheter and does not address the key mechanisms required of a functioning valve. Additionally, the device requires intraluminal-securing means such as suturing to anchor the device at the desired location.

The Taheri valve describes an aortic valve replacement combined with an aortic arch graft. The devices and percutaneous methods described require puncture of the chest cavity.

Anderson has disclosed various balloon expandable percutaneous prosthetic valves. The latest discloses a valve prosthesis comprised of a stent made from an expandable cylindrical structure made of several spaced apices and an elastically collapsible valve mounted to the stent with the commissural points of the valve mounted to the apices. The device is placed at the desired location by balloon expanding the stent and valve. The main disadvantage to this design is the 20+ French size delivery requirement. Other problems include anchoring stability, perivalvular leakage, difficult manufacture and suspect valve performance.

The Jayaraman valve includes a star-shaped stent and a replacement valve and/or replacement graft for use in repairing a damaged cardiac valve. The device is comprised of a chain of interconnected star-shaped stent segments in the center of which sits a replacement valve. The flow-regulation mechanism consists of three flaps cut into a flat piece of graft material that is rolled to form a conduit in which the three flaps may be folded inwardly in an overlapping manner. An additional flow-regulation mechanism is disclosed in which a patch (or multiple patches) is sutured to the outside of a conduit which is then pulled inside out or inverted such that the patch(s) reside on the fully inverted conduit. A balloon catheter is required to assist expansion during delivery. The disadvantages of this design include lack of sufficient anchoring mechanism; problematic interference concerns with adjacent tissues and anatomical structures; fatigue concerns associated with the multiplicity of segments, connections and sutures; lack of an adequately controlled and biased flow-regulation mechanism; uncertain effective valve orifice, difficult manufacture; balloon dilation requirement; complex, difficult and inaccurate delivery and large delivery profile.

The Besseler valve discloses methods and devices for the endovascular removal of a defective heart valve and the replacement with a percutaneous cardiac valve. The device is comprised of a self-expanding stent member with a flexible valve disposed within. The stent member is of a self-expanding cylindrical shape made from a closed wire in formed in a zigzag configuration that can be a single piece, stamped or extruded or formed by welding the free ends together. The flow-regulation mechanism is comprised of an arcuate portion which contains a slit (or slits) to form leaflets and a cuff portion which is sutured to and encloses the stent. The preferred flow regulator is a porcine pericardium with three cusps. An additional flow regulator is described in which the graft material that comprises the leaflets (no additional mechanisms for flow-regulation) extends to form the outer cuff portion and is attached to the stent portion with sutures. The anchoring segment is provided by a plurality of barbs carried by the stent (and therefor penetrating the cuff-graft segment). Delivery requires endoluminal removal of the natural valve because the barb anchors will malfunction if they are orthotopically secured to the native leaflets instead of the more rigid tissue at the native annulus or vessel wall. Delivery involves a catheter within which the device and a pusher rod are disposed. The disadvantages of the device are lack of a well defined and biased flow-regulation mechanism, anatomic valve removal is required thereby lengthening the procedure time, increasing difficulty and reducing clinical practicality, trauma-inducing barbs as described above and the device is unstable and prone to migration if barbs are omitted.

The Khosravi valve discloses a percutaneous prosthetic valve comprised of a coiled sheet stent similar to that described by Derbyshire, U.S. Pat. No. 5,007,926, to which a plurality of flaps are mounted on the interior surface to form a flow-regulation mechanism that may be comprised of a biocompatible material. The disadvantages of this design include problematic interactions between the stent and flaps in the delivery state, lack of clinical data on coiled stent performance, the lack of a detailed mechanism to ensure that the flaps will create a competent one-directional valve, lack of appropriate anchoring means, and the design requirements imposed by surrounding anatomical structures are ignored.

The Zadno-Azizi valve discloses a device in which flow-regulation is provided by a flap disposed within a frame structure capable of taking an insertion state and an expanded state. The preferred embodiment of the flow-regulation mechanism is defined by a longitudinal valve body made of a sufficiently resilient material with a slit(s) that extends longitudinally through the valve body. Increased sub-valvular pressure is said to cause the valve body to expand thereby opening the slit and allowing fluid flow there through. The valve body extends into the into the lumen of the body passage such that increased supra-valvular pressure will prevent the slit from opening thereby effecting one-directional flow. The device includes embedding the frame within the seal or graft material through injection molding, blow molding and insertion molding. The disadvantages of the device include the flow-regulation mechanism provides a small effective valve orifice, the turbidity caused by the multiple slit mechanisms, the large delivery profile required by the disclosed embodiments and the lack of acute anchoring means.

Finally, the Leonhardt valve is comprised of a tubular graft having radially compressible annular spring portions and a flow regulator, which is preferably a biological valve disposed within. In addition to oversizing the spring stent by 30%, anchoring means is provided by a light-activated biocompatible tissue adhesive is located on the outside of the tubular graft and seals to the living tissue. The stent section is comprised of a single piece of superelastic wire formed into a zigzag shape and connected together by crimping tubes, adhesives or welds. A malleable thin-walled, biocompatible, flexible, expandable, woven fabric graft material is connected to the outside of the stent that is in turn connected to the biological flow regulator. Disadvantages of this device include those profile concerns associated with biological valves and unsupported graft-leaflet regulators, a large diameter complex delivery system and method which requires multiple anchoring balloons and the use of a light activated tissue adhesive in addition to any prior valvuloplasty performed, interference with surrounding anatomy and the questionable clinical utility and feasibility of the light actuated anchoring means.

SUMMARY OF THE INVENTION

With the shortcomings of the prior art devices, there remains a need for a clinically effective endoluminally deliverable prosthetic valve that is capable of orthotopic delivery, provides a mechanically defined, biased and hemodynamically sound flow-regulation mechanism, provides sufficient force to maintain a large acute effective valvular orifice dimension which expands to a known larger effective orifice dimension, compliant with adjacent dynamic anatomical structures, does not require valve removal, does not require chronic anticoagulation treatment, meets regulatory fatigue requirements for cardiac valve prostheses, provides a low-metal high-strength stent-annulus, is surgically explantable or endoluminally removable, in addition to being able to deploy multiple valves orthotopically, provides a delivery profile which does not exceed the 12 French size suitable for peripheral vascular endoluminal delivery, combines anatomic valve exclusion and prosthetic valve delivery via a single catheter delivery system and with short duration atraumatic procedure which is easy to complete and beneficial to very sick patients.

The embodiments disclosed herein provide a prosthetic endoluminally-deliverable unidirectional valve. The embodiments disclosed herein have multiple configurations to treat malfunctioning anatomical valves including heart and venous valves. Prosthetic cardiac valve configurations include the chamber-to-vessel for orthotopic placement at the valvular junction between a heart chamber and a vessel, and the chamber-to-chamber for orthotopic placement at the valvular junction between two heart chambers or for septal defect repair where a septal occluding member is substituted for the flow regulator valve flaps. Prosthetic venous valve configurations include the vessel-to-vessel for orthotopic or non-orthotopic placement at a valvular junction within a vessel.

The embodiments disclosed herein consist generally of a stent body member, a graft, and valve flaps. The stent body member may be fashioned by laser cutting a hypotube or by weaving wires into a tubular structure, and is preferably made from shape memory or super-elastic materials, such as nickel-titanium alloys known as NITINOL, but may be made of balloon expandable stainless steel or other plastically deformable stent materials as are known in the art, such as titanium or tantalum, or may be self-expanding such as by weaving stainless steel wire into a stressed-tubular configuration in order to impart elastic strain to the wire. The graft is preferably a biocompatible, fatigue-resistant membrane which is capable of endothelialization, and is attached to the stent body member on at least portions of either or both the lumenal and ablumenal surfaces of the stent body member by suturing to or encapsulating stent struts. The valve leaflets are preferably formed by sections of the graft material attached to the stent body member.

The stent body member is shaped to include the following stent sections: proximal and distal anchors, a intermediate annular stent section, and at least one valve arm or blood flow regulator struts. The proximal and distal anchor sections are present at opposing ends of the prosthesis and subtend either an acute, right or obtuse angle with a central longitudinal axis that defines the cylindrical prosthesis. In either the CV or CC configurations, the proximal anchor is configured to assume approximately a right angle radiating outward from the central longitudinal axis of the prosthesis in a manner which provides an anchoring flange. When being delivered from a delivery catheter, the proximal anchor is deployed first and engages the native tissue and anatomical structures just proximal to the anatomic valve, such as the left ventricle wall in the case of retrograde orthotopic delivery at the aortic valve. Deployment of the proximal anchor permits the intermediate annular stent section to be deployed an reside within the native valve annular space and the ablumenal surface of the intermediate annular stent section to abut and outwardly radially compress the anatomic valve leaflets against the vascular wall. The distal anchor is then deployed and radially expands to contact the vascular wall and retain the prosthesis in position, thereby excluding the anatomic valve leaflets from the blood flow and replacing them with the prosthetic valve leaflets.

Flow regulation in the inventive stent valve prosthesis is provided by the combination of the prosthetic valve leaflets and the valve arms and is biased closed in a manner similar manner to that described for a surgically implanted replacement heart valve by Boretos, U.S. Pat. No. 4,222,126. The valve regulator-struts are preferably configured to be positioned to radiate inward from the stent body member toward the central longitudinal axis of the prosthesis. The graft-leaflet has the appearance of a partially-everted tube where the innermost layer, on the lumenal surface of the stent body member, forms the leaflets and the outer-most layer, on the ablumenal surface of the stent body member, forms a sealing graft which contacts and excludes the immobilized anatomical valve leaflets. The struts of the stent are encapsulated by the outer graft-membrane. The valve regulator-struts are encapsulated by the inner leaflet-membrane and serve to bias the valve to the closed position. The regulator-struts also prevent inversion or prolapse of the otherwise unsupported leaflet-membrane during increased supra-valvular pressure. The inner leaflet-membrane may also be attached to the outer graft-membrane at points equidistant from the valve strut-arms in a manner analogous to that described for a surgically implanted replacement heart valve by Cox, U.S. Pat. No. 5,824,063. The combination of the thin walled properties of the leaflet-membrane, the one-sided open lumen support of the intermediate annular stent section, the free ends of the valve leaflets, the biasing and support provided by the valve regulator-struts and the attachment points all work to provide a prosthetic valvular device capable of endoluminal delivery which simulates the hemodynamic properties of a healthy anatomical cardiac or venous valve.

BRIEF DESCRIPTION OF FIGURES

FIG. 1 is a perspective view of the inventive valve stent chamber-to-vessel embodiment in its fully deployed state.

FIG. 2 is a perspective view of the inventive valve stent chamber-to-vessel embodiment in its fully deployed state with the outermost graft layer and stent layer partially removed to show an embodiment of the valve apparatus.

FIG. 3 is a top view of the inventive valve stent chamber-to-vessel embodiment in its fully deployed state.

FIG. 4 shows the cross-sectional taken along line 4-4 of FIG. 1.

FIG. 5 is a bottom view of the inventive valve stent chamber-to-vessel embodiment in its fully deployed state.

FIG. 6A illustrates a cross-sectional view of a human heart during systole with the inventive valve stent chamber-to-vessel embodiment implanted in the aortic valve and illustrating a blood flow vector of an ejection fraction leaving the left ventricle and passing through the inventive valve stent.

FIG. 6B illustrates a cross-sectional view of a human heart during diastole with the inventive valve stent chamber-to-vessel embodiment implanted in the aortic valve and illustrating a blood flow vector of blood passing from the left atrium, through the mitral valve and into the left ventricle during and a retrograde blood flow vector blocked by the inventive valve stent in the aorta.

FIG. 12A illustrates a cross-sectional view of a human heart during atrial systole with the inventive valve stent chamber-to-chamber embodiment implanted at the site of the mitral valve and illustrating a blood flow vector of a filling fraction leaving the left atrium and entering the left ventricle.

FIG. 12B illustrates a cross-sectional view of a human heart during atrial diastole with the inventive valve stent chamber-to-chamber embodiment implanted at the site of the mitral valve and illustrating a blood flow vector of an ejection fraction from the left ventricle to the aorta and the back pressure against the implanted mitral valve prosthesis.

FIG. 18A and 18B show cross-sectional views of a vein and venous valve illustrating the inventive prosthetic venous valve in the open and closed state.

FIG. 19 is a cross-sectional diagrammatic view of a valvuloplasty and stent valve delivery catheter in accordance with the embodiments disclosed herein.

FIGS. 20A-20I are diagrammatic cross-sectional views illustrating single catheter valvuloplasty, inventive stent valve delivery and stent valve operation in situ in accordance with the method of the embodiments disclosed herein.

DETAILED DESCRIPTION OF THE PREFERRED EMBODIMENTS

Figure 7:
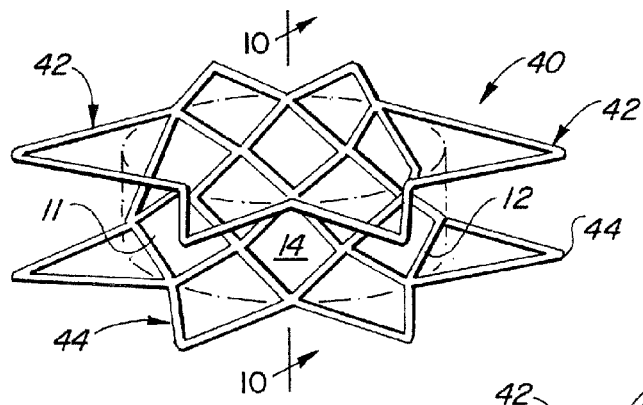
FIG. 7 is a perspective view of the inventive valve stent chamber-to-chamber embodiment in its fully deployed state.
Figure 8:
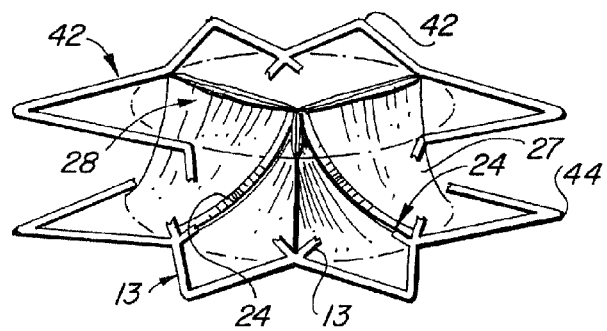
FIG. 8 is a is a perspective view of the inventive valve stent chamber-to-chamber embodiment in its fully deployed state with the outermost graft layer and stent layer partially removed to show an embodiment of the valve apparatus.
Figure 9:
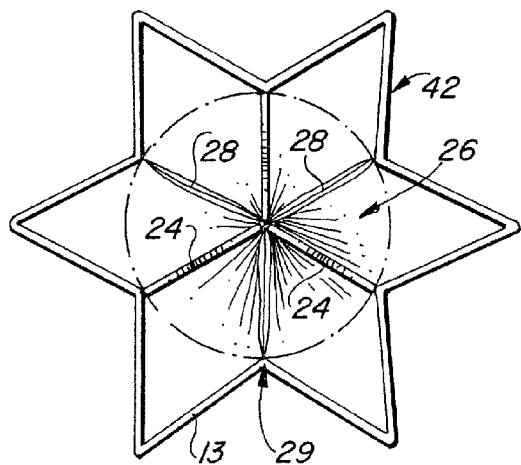
FIG. 9 is a top view of the inventive valve stent chamber-to-chamber embodiment in its fully deployed state.
Figure 10:
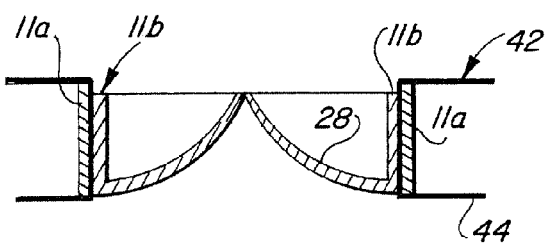
FIG. 10 shows the cross sectional view taken along line 10-10 of FIG. 7.
Figure 11:
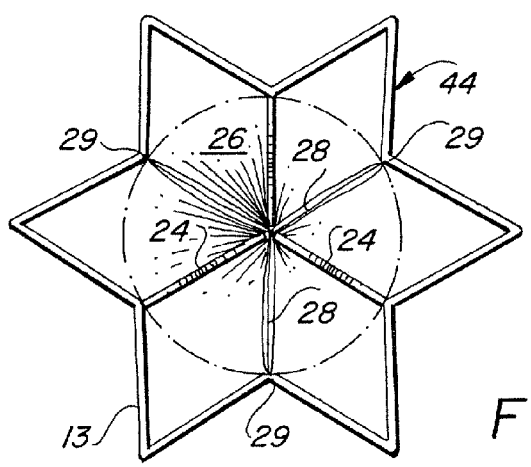
FIG. 11 is a bottom view of inventive valve stent chamber-to-chamber embodiment in its fully deployed state.
Figure 13:
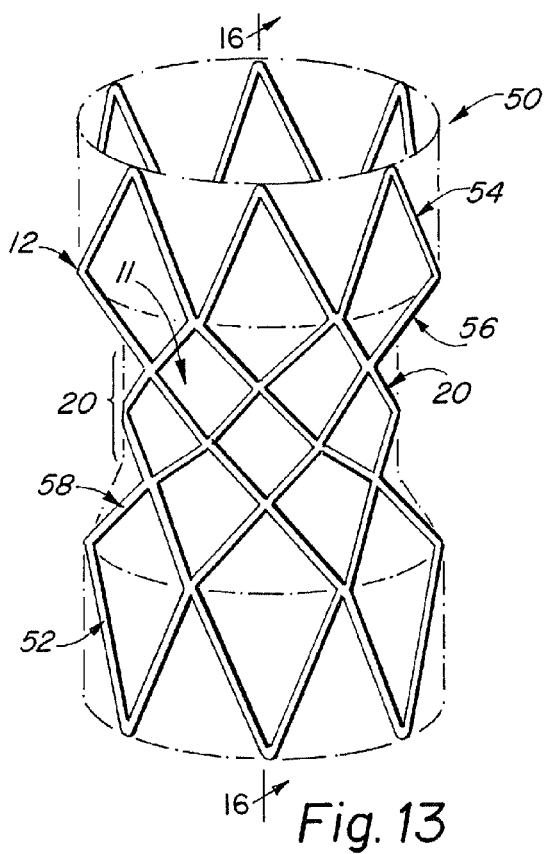
FIG. 13 is a perspective view of the chamber-to-vessel configuration in the fully deployed state.
Figure 15:
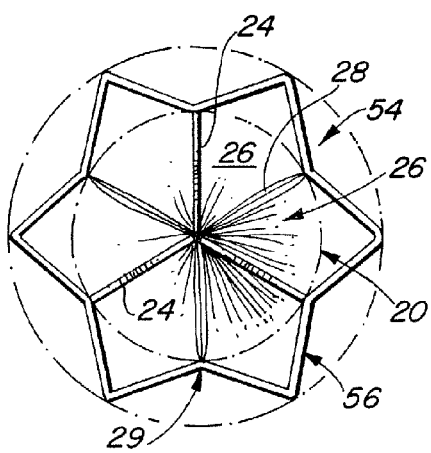
FIG. 15 is a top view of the same configuration.
Figure 14:
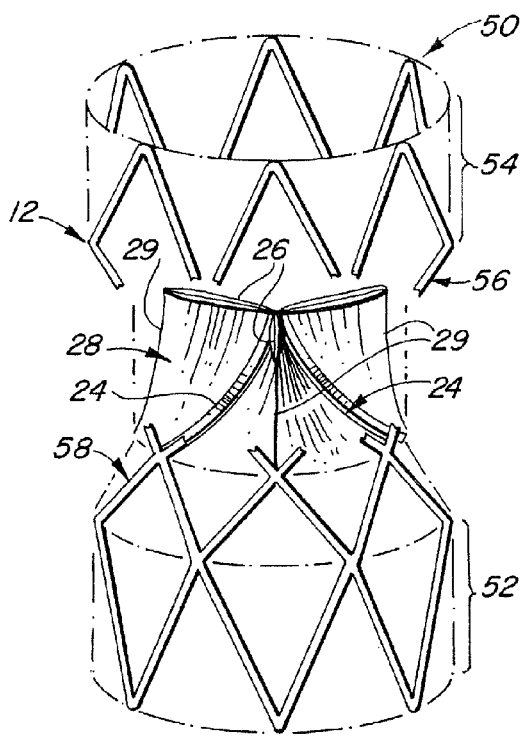
FIG. 14 is a perspective view of the same configuration in the fully deployed state with the outermost graft layer and stent layer partially removed to show an embodiment of the valve apparatus.
Figure 16:
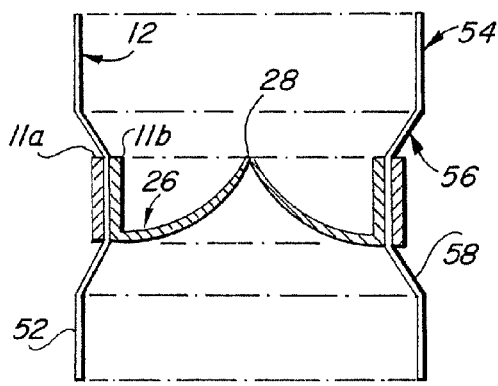
FIG. 16 shows the cross sectional view of the same configuration for the deployed state.
Figure 17:
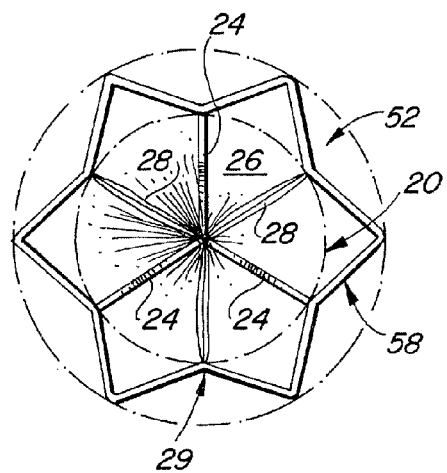
FIG. 17 is a bottom view of the same configuration.

The prosthetic valves of the embodiments disclosed herein are well-suited for cardiac delivery via a femoral or subclavian artery approach using a delivery catheter, and, depending upon the specific configuration selected, may be deployed within the heart to repair valve defects or disease or septal defects or disease. According to one embodiment, there is provided a chamber-to-vessel (CV) configuration which is particularly well-suited as an aortic valve prosthesis to facilitate blood flow from the left ventricle to the aorta. In a second embodiment, there is provided a prosthetic valve in a chamber-to-chamber (CC) configuration which is particularly well-adapted for mitral valve replacement or repair of septal defects. Finally, a third embodiment is provided in a vessel-to-vessel (VV) configuration, which is well suited for venous valve exclusion and replacement.

Common to each of the CV, CC and VV embodiments are a stent support member, a graft member which covers at least a portion of either or both the lumenal and ablumenal surfaces of the stent, valve flaps which are formed either by biological xenograft valves, synthetic valves formed from either the same material or a different material as the graft member, the valve flaps being coupled to the stent in a manner which biases the valve flaps so they close upon a zero pressure differential across the valve region.

The embodiments disclosed herein provide orientational definitions. For purposes of the embodiments disclosed herein, references to positional aspects of the present invention will be defined relative to the directional flow vector of blood flow through the implantable device. Thus, the term "proximal" is intended to mean on the inflow or upstream flow side of the device, while "distal" is intended to mean on the outflow or downstream flow side of the device. With respect to the catheter delivery system described herein, the term "proximal" is intended to mean toward the operator end of the catheter, while the term "distal" is intended to mean toward the terminal end or device-carrying end of the catheter.

The embodiments disclosed herein comprises generally of three preferred embodiments, each embodiment corresponding to a prosthetic stent valve configuration adapted for either heart chamber to blood vessel communication, chamber to chamber communication or vessel to vessel, or intravascular configuration. Certain elements are common to each of the preferred embodiments of the invention, specifically, each embodiment includes a stent body member which defines a central annular opening along the longitudinal axis of the stent body member, a graft member which covers at least a portion of the stent body member along either the lumenal or ablumenal surfaces of the stent body member, at least one biasing arm is provided and projects from the stent body member and into the central annular opening of the stent body member, and at least one valve flap member which is coupled to each biasing arm such that the biasing arm biases the valve flap member to occlude the central annular opening of the stent body member under conditions of a zero pressure differential across the prosthesis. The stent body member is preferably made of a shape memory material or superelastic material, such as NITINOL, but also be fabricated from either plastically deformable materials or spring-elastic materials such as is well known in the art. Additionally, the stent body member has three main operable sections, a proximal anchor section, a distal anchor section and an intermediate annular section which is intermediate the proximal and distal anchor sections. Depending upon the specific inventive embodiment, the distal and proximal anchor sections may be either a diametrically enlarged section or may be a flanged section. The intermediate annular section defines a valve exclusion region and primary blood flow channel of the inventive valve stent. The intermediate annular section defines a lumenal opening through which blood flow is established. The transverse cross-section of the lumenal opening may be circular, elliptical, ovular, triangular or quadralinear, depending upon the specific application for which the valve stent is being employed. Thus, for example, where a tricuspid valve is particularly stenosed, it may be preferable to employ a valve stent with a lumenal opening in the intermediate annular section which has a triangular transverse cross-sectional dimension.

Chamber-to-Vessel Configuration

An implantable prosthesis or prosthetic valve in accordance with certain embodiments of the chamber-to-vessel CV configuration is illustrated generally in FIGS. 1-5. The chamber-to-vessel valve stent 10 consists of an expandable stent body member 12 and graft member 11. The stent body member 12 is preferably made from a shape memory and/or superelastic NITINOL material, or thermomechanically similar materials, but may be made of plastically deformable or elastically compliant materials such as stainless steel, titanium or tantalum. The graft member 11 is preferably made of biologically-derived membranes or biocompatible synthetic materials such as DACRON or expanded polytetrafluoroethylene. The stent body member 12 is configured to have three functional sections: a proximal anchor flange 22, an intermediate annular section 20 and a distal anchor section 16. The stent body member 12, as with conventional stents is formed of a plurality of stent struts 13 which define interstices 14 between adjacent stent struts 13. The stent body member preferably also includes a transitional section 18 which interconnects the intermediate annular section 20 and the distal anchor section 16, which together define a valve exclusion region of the inventive stent valve 10 to exclude the anatomic valve after implantation. The proximal anchor flange 22, the intermediate annular section 20 and the distal anchor section 16 are each formed during the formation of the stent body member and are formed from the same material as the stent body member and comprise stent struts 13 and intervening interstices 14 between adjacent pairs of stent struts 13. The anchor flange 22, for example, consists of a plurality of stent struts and a plurality of stent interstices, which project radially outwardly away from the central longitudinal axis of the stent body member. Thus, the different sections of the stent body member 12 are defined by the positional orientation of the stent struts and interstices relative to the central longitudinal axis of the stent body member 12.

With reference to FIG. 2, there is shown in greater detail the valve body 26 and valve arms or flow regulator struts 24 coupled to the stent body member 12. The valve body 26 subtends the central annular opening of the stent valve 10 and is illustrated in its closed position. In accordance with one embodiment, the graft member 11 consists of an outer or ablumenal graft member 11a and an inner or lumenal graft member 11b. The outer graft member 11a encloses at least a portion of the ablumenal surface of the intermediate annular section 20 of the stent body member, while the inner graft member 11b is coupled, on the lumenal surface of the intermediate annular section 20 of the stent body member 12, to the outer graft member 11a through the interstices 14 of the stent body member. The valve body 26 is formed by everting the inner graft member 11b toward the central longitudinal axis of the stent body member 12 such that free ends or valve flap portions 28 of the inner graft member 11b are oriented toward the distal anchor section 16 of the stent body member 12 and a pocket or envelope 27 is formed at the eversion point of the inner graft member 11b adjacent the junction between the intermediate annular section 20 and the proximal anchor flange 22 of the stent body member 12. Alternatively, portions of the outer graft member 11a may be passed through to the lumenal surface of the stent body member 12, thereby becoming the inner graft member 11b and everted to form the valve body 26.

Valve arms or regulator struts 24 are coupled or formed integral with the stent body member 12 and are positioned adjacent the junction point between intermediate annular section 20 and the proximal anchor flange 22 of the stent body member 12. The valve arms 24 are oriented radially inward toward the central longitudinal axis of the stent body member 12 when in their zero strain state. The valve arms 24 are attached or coupled to the valve flap portions 28 of the inner graft member leaflets to bias the valve flap portions 28 to the closed position when under zero pressure differential across the stent valve 10.

The zero strain position of the valve arms 24 is radially inward and orthogonal to the central longitudinal axis of the stent valve 10. Valve arms 24 have a length which is preferably longer than the radius of the lumenal diameter of the stent valve 10, and they extend distally into the lumen of the stent valve 10 such that, in conjunction with the action of the valve leaflets 28, the valve arms 24 are prevented from achieving their zero strain configuration thereby biasing the valve closed. As shown in FIG. 4, the valve arms 24 force the valve leaflets 28 to collapse into the center of the lumen of the stent valve 10, thus biasing the valve to its closed position.

It is preferable to couple sections of the valve flaps 28, along a longitudinal seam 29, to the inner graft member 11b and the outer graft member 11a at points equidistant from the valve arms 24 in order to impart a more cusp-like structure to the valve flaps 28. It should be appreciated, that the graft member 11 should cover at least a portion of the abluminal surface of the stent body member 12 in order to exclude the anatomic valves, but may also cover portions or all of the stent valve member 12, including the distal anchor section 16, the intermediate annular section 20, the transition section 18 and/or the proximal anchor flange 22, on either or both of the lumenal and abluminal surfaces of the stent body member.

In accordance with a particularly preferred embodiment of the CV valve stent 10, the proximal anchor flange 22, which consists of a plurality of stent struts and stent interstices which project radially outward away from the central longitudinal axis of the valve stent 10, is configured to have one or more stent struts eliminated from the proximal anchor flange 22 to define an open region which is positioned in such a manner as to prevent the CV valve stent 10 from interfering with or impinging upon an adjacent anatomic structure. For example, where the CV valve stent 10 is to be an aortic valve prosthesis, it is known that the mitral valve is immediately adjacent the aortic valve, and the mitral valve flaps deflect toward the left ventricle. Thus, placing the CV valve stent 10 such that the proximal anchor flange 22 is adjacent the mitral valve might, depending upon the particular patient anatomy, interfere with normal opening of the mitral valve flaps. By eliminating one or more of the stent struts in the proximal anchor flange 22, an opening is created which permits the mitral valve flaps to deflect ventricularly without impinging upon the proximal anchor flange 22 of the CV valve stent 10.

Similarly, the stent struts of the CV valve stent 10 may be oriented in such a manner as to create interstices of greater or smaller area between adjacent struts, to accommodate a particular patient anatomy. For example, where the stent struts in the distal anchor section 16 would overly an artery branching from the aorta, such as the coronary ostreum arteries, it may be desirable to either eliminate certain stent struts, or to configure certain stent struts to define a greater interstitial area to accommodate greater blood flow into the coronary ostreum.

In the case of providing an oriented opening in the proximal anchor flange, or an oriented opening in the interstitial spaces of the distal anchor, it is desirable to provide radiopaque markers on the stent body member 12 to permit the CV valve stent to be oriented correctly relative to the anatomic structures.

FIGS. 6A and 6B illustrate the inventive CV stent valve 10 implanted in the position of the aortic valve and excluding the anatomic aortic valve AV. FIG. 6A illustrates the heart during systole in which a positive pressure is applied to the prosthetic aortic valve by contraction of the left ventricle LV and the ejection fraction represented by the arrow. The systolic pressure overcomes the bias exerted by the valve arms 24 and causes the valve leaflets 26 to open and release the ejection fraction into the aorta. FIG. 6B illustrates that the presence of a negative pressure head across the stent valve 10, i.e. such as that during diastole, causes the biased valve leaflets 26 which are already closed, to further close, and prevent regurgitation from the aorta into the left ventricle.

Chamber-to-Chamber Configuration

FIGS. 7-11 illustrate the inventive stent valve in the chamber-to-chamber (CC) configuration 40. The CC valve stent 40 is constructed in a manner which is virtually identical to that of the CV valve stent 10 described above, except that the distal anchor section 16 of the CV valve stent 10 is not present in the CC valve stent 40, but is substituted by a distal anchor flange 42 in the CC stent valve. Thus, like the CV valve stent 10, described above, the CC valve stent 40 if formed of a stent body member 12 and a graft member 11, with the graft member having lumenal 11b and ablumenal 11a portions which cover at least portions of the lumenal and abluminal surfaces of the stent body member 12, respectively. The CC valve stent 40 has both a proximal anchor flange 44 and a distal anchor flange 42 which are formed of sections of the stent body member 12 which project radially outward away from the central longitudinal axis of the CC valve stent 40 at opposing ends of the stent body member 12.

Like the CV valve stent 10, the lumenal graft portion 11b is everted inwardly toward the central longitudinal axis of the valve stent 40 and free ends 28 of the lumenal graft portion 11b to form valve flaps 26 which project distally toward distal anchor flange 42. Flow regulation struts 24 are coupled to or integral with the proximal anchor flange 44 and intermediate annular section 20 and project radially inward toward the central longitudinal axis of the CC valve stent 40. The valve flaps 26 are coupled to the flow regulation struts 24 and the flow regulation struts 24 bias the valve flaps 26 to a closed position under a zero strain load.

Like with the CV stent valve 10, it is preferable to couple sections of the valve flaps 28, along a longitudinal seam 29, to the inner graft member 11b and the outer graft member 11a at points equidistant from the valve arms 24 in order to impart a more cusp-like structure to the valve flaps 28.

Turning to FIGS. 12A and B there is illustrated the inventive CC stent valve 40 implanted in the position of the mitral valve and excluding the anatomic mitral valve MV. FIG. 12A illustrates the heart during atrial systole in which a positive pressure is applied to the prosthetic mitral valve by contraction of the left atrium LA and the pressure exerted by the blood flow represented by the arrow. The atrial systolic pressure overcomes the bias exerted by the valve arms 24 onto the valve leaflets 26, and causes the valve leaflets 26 to open and release the atrial ejection fraction into the left ventricle. FIG. 12 B illustrates that the presence of a negative pressure head across the stent valve 40, i.e. such as that during atrial diastole, causes the biased valve leaflets 26 which are already closed, to further close, and prevent backflow from the left ventricle into the left atrium.

In accordance with another embodiment, the CC configuration may be adapted for use in repairing septal defects. By simply substituting a membrane for the valve leaflets 26, the lumen of the stent body member 12 is occluded. The CC stent valve 40 may be delivered endoluminally and placed into a position to subtend a septal defect and deployed to occlude the septal defect.

Vessel to Vessel Configuration

Turning now to FIGS. 13-17, there is illustrated the inventive stent valve in its vessel-to-vessel (VV) valve stent configuration 50. The VV valve stent 50 is constructed in a manner which is virtually identical to that of the CV valve stent 10 described above, except that the proximal anchor flange 22 of the CV valve stent 10 is not present in the VV valve stent 50, but is substituted by a proximal anchor section 52 in the VV stent valve. Thus, like the CV valve stent 10, described above, the VV valve stent 50 is formed of a stent body member 12 and a graft member 11, with the graft member having lumenal 11b and ablumenal 11a portions which cover at least portions of the lumenal and ablumenal surfaces of the stent body member 12, respectively. The VV valve stent 50 has both a proximal anchor section 52 and a distal anchor section 54 which are formed of sections of the stent body member 12 which are diametrically greater than the intermediate annular section 20 of the VV valve stent 50. Transition sections 56 and 58 taper outwardly away from the central longitudinal axis of the VV valve stent 50 and interconnect the intermediate annular section 20 to each of the distal anchor section 54 and the proximal anchor section 52, respectively.

Like the CV valve stent 10, in the VV valve stent 50, the graft member 11, particularly the lumenal graft portion 11b or the ablumenal graft portion 11a, or both, is everted inwardly toward the central longitudinal axis of the valve stent 40 and free ends 28 of the lumenal graft portion 11b to form valve flaps 26 which project distally toward distal anchor flange 42. Flow regulation struts 24 are coupled to or integral with the stent body member at the proximal transition section 58 and project radially inward toward the central longitudinal axis of the VV valve stent 50. The valve flaps 26 are coupled to the flow regulation struts 24 and the flow regulation struts 24 bias the valve flaps 26 to a closed position under a zero strain load. Like with the CV stent valve 10 and the CC stent valve 40, it is preferable to couple sections of the valve flaps 28, along a longitudinal seam 29, to the inner graft member 11b and the outer graft member 11a at points equidistant from the valve arms 24 in order to impart a more cusp-like structure to the valve flaps 28.

Turning to FIGS. 18A and B there is illustrated the inventive VV stent valve 50 implanted in the position of a venous valve and excluding the anatomic venous valve flaps VE. FIG. 18A illustrates the vein under systolic blood pressure in which a positive pressure is applied to the prosthetic venous valve and the pressure exerted by the blood flow represented by the arrow. The systolic pressure overcomes the bias exerted by the valve arms 24 onto the valve leaflets 26, and causes the valve leaflets 26 to open and permit blood flow through the prosthesis. FIG. 18B illustrates that the presence of a negative pressure head across the VV stent valve 50, i.e. such as which exists at physiological diastolic pressures, causes the biased valve leaflets 26 which are already closed, to further close, and prevent backflow from the left ventricle into the left atrium.

The purpose of the proximal 54 and distal 52 anchor sections of the stent body member 12 is to anchor the prosthesis at the anatomic vessel-vessel junction, such as a venous valve, while causing minimal interference with adjacent tissue. The intermediate annular section 20 of the VV stent valve 50 excludes diseased anatomic leaflets and surrounding tissue from the flow field. The flare angle of the transition sections 56, 58 between the intermediate annular section 20 and each of the proximal and distal anchor sections 54, 52, respectively, may be an acute angle, a right angle or an obtuse angle, depending upon the anatomical physiological requirements of the implantation site. Alternatively, the transition sections 56, 58 may be coplanar with the proximal and distal anchor section 52, 54, respectively, thereby, eliminating any transition flare angle, depending upon the anatomical and physiological requirements of the delivery site.

Single Catheter Valvuloplasty Stent Valve Delivery System and Method of Delivery In accordance with another embodiment, there is also a single catheter valvuloplasty and valve stent delivery system 200 illustrated in FIG. 19. The objective of the single catheter delivery system 200 is to permit the surgeon or interventionalist to percutaneously deliver and deploy the inventive valve stent 10, 40 or 50 at the desired anatomical site and to perform valvuloplasty with a single catheter. In accordance with the preferred embodiment of the single catheter delivery system 200, there is provided a catheter body 210 having dual lumens 212, 216. A first lumen 212 is provided as a guidewire lumen and is defined by a guidewire shaft 222 which traverses the length of the catheter body 210. A second lumen is an inflation lumen 216 for communicating an inflation fluid, such as saline, from an external source, through an inflation port 240 at the operator end of the catheter 210, to an inflatable balloon 214 located at or near the distal end of the catheter body 210. The inflation lumen 216 is defined by an annular space between the lumenal surface of the catheter body 210 and the ablumenal surface of the guidewire shaft 222. A capture sheath 217 is provided at the distal end 215 of the catheter body 210 and is positioned adjacent and distal the balloon 214. The capture sheath 217 defines an annular space about the guidewire lumen 212 and the capture sheath 217 into which the stent valve 10, 40 or 50 is positioned and retained during delivery. An annular plug member 220 is within the inflation lumen 216 distal the balloon 214 and terminates the inflation lumen 216 in a fluid tight manner. Annular plug member 220 has a central annular opening 221 through which the guidewire shaft 222 passes. The annular plug member 220 is coupled to the guidewire shaft 222 and is moveable axially along the central longitudinal axis of the catheter 200 by moving the guidewire shaft 222. The annular plug member 220 also serves to abut the stent valve 10, 40 and 50 when the stent valve 10, 40 and 50 is positioned within the capture sheath 217. The guidewire shaft 222 passes through the capture sheath 217 and terminates with an atraumatic tip 218 which facilitates endoluminal delivery without injuring the native tissue encountered during delivery. With this configuration, the stent valve is exposed by proximally withdrawing the catheter body 210, while the guidewire shaft 222 is maintained in a fixed position, such that the annular plug member 220 retains the position of the stent valve as it is uncovered by capture sheath 217 as the capture sheath 217 is being proximally withdrawn with the catheter body 210.

In many cases the anatomic valve will be significantly stenosed, and the valve flaps of the anatomic valve will be significantly non-compliant. The stenosed valves may be incapable of complete closure permitting blood regurgitation across the anatomic valve. Thus, it may be desirable to configure the inflatable balloon 214 to assume an inflation profile which is modeled to maximally engage and dilatate the anatomic valves. For example, a tricuspid valve, such as the aortic valve may stenose to an opening which has a generally triangular configuration. In order to maximally dilatate this triangular opening, it may be desirable to employ a balloon profile which assumes a triangular inflation profile. Alternatively, it may be advantageous to configure the balloon such that it does not fully occlude the anatomic lumen when inflated, but permits a quantum of blood flow to pass around the balloon in its inflated state. This may be accomplished by providing channels or ridges on the ablumenal surface of the balloon. Additionally, irregular inflation profiles of the balloon may facilitate continuous blood flow about the inflated balloon. Furthermore, it may be desirable to configure the balloon to have an hour-glass inflation profile to prevent migration or slippage of the balloon in the anatomic valve during valvuloplasty.

In accordance with one embodiment, it is preferable that the capture sheath 217 be made of a material which is sufficiently strong so as prevent the stent valve 10, 40, 50 from impinging upon and seating into the capture sheath 217 due to the expansive pressure exerted by the stent valve 10, 40, 50 against the capture sheath. Alternatively, the capture sheath 217 may be lined with a lubricious material, such as polytetrafluoroethylene, which will prevent the capture sheath 217 from exerting drag or frictional forces against the stent valve during deployment of the stent valve.

In accordance with another embodiment, it is also contemplated that the position of the balloon 214 and the capture sheath 217 may be reversed, such that the balloon 214 is distal the capture sheath 217. In this configuration, the anatomic valve may be radially enlarged by dilatating the balloon 214, then the catheter moved distally to position the capture sheath 217 at the anatomic valve and deployed in the manner described above. This would also allow for post-deployment balloon expansion of the deployed stent valve without the need to traverse the prosthetic valve in a retrograde fashion. Alternatively, the catheter 200 may be provided without a balloon 214 in those cases where valvuloplasty is not required, e.g., where a stenotic valve does not need to be opened such as with a regurgitating valve, and the catheter 200 is terminated at its distal end with only a capture sheath 217, and deployment occurs as described above.

Figure 20C:
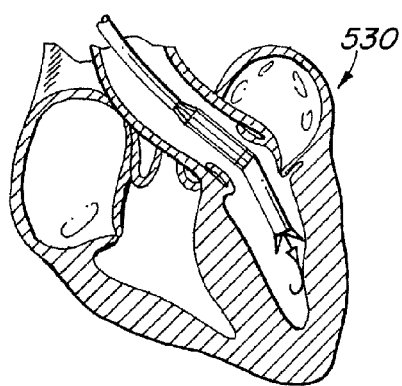
Figure 20D:
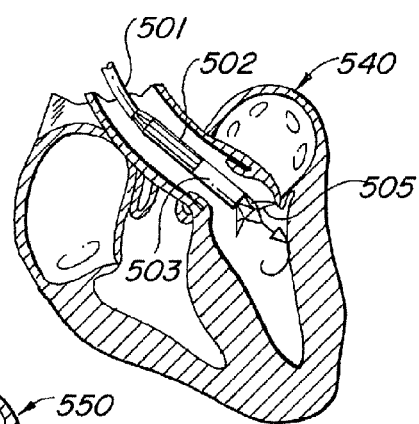
Figure 20E:
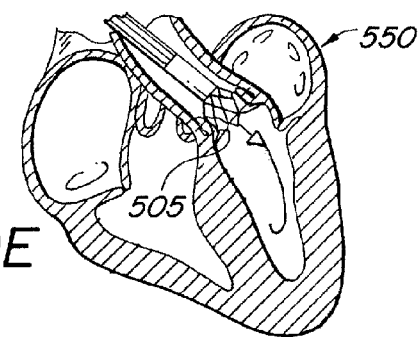
Figure 20F:
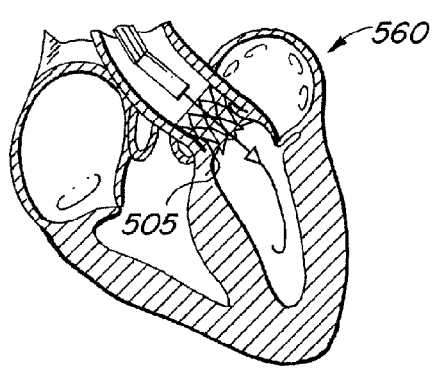
Figure 20G:
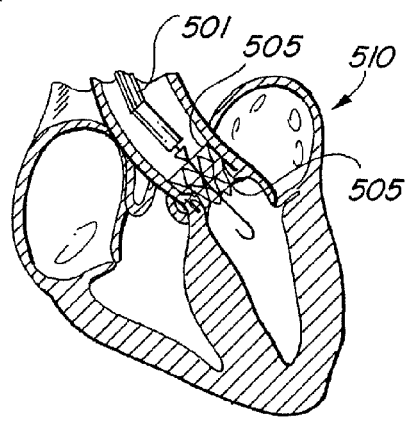
Figure 20H:
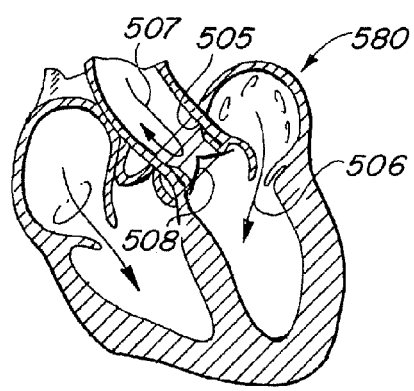
Figure 20I:
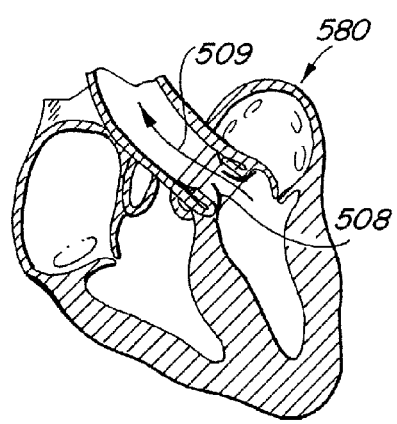

Turning now to FIGS. 20A-20I there is illustrated the sequence of steps in delivery of the stent valve, valvuloplasty of the aortic valve and deployment of the stent valve at the position of the aortic valve. The single catheter delivery system 501 having a distal balloon 502 and a capture sheath 503 covering the valve stent 10 (not shown in FIGS. 20A-B), is delivered percutaneously either through a femoral or subclavian artery approach, and traverses the aorta and is passed through the aortic valve 510 such that the balloon 503 on the distal end of catheter 501 is adjacent the aortic valve 510 and the capture sheath 503 is within the left ventricle 504. A valvuloplasty step 520 is performed by inflating balloon 503 to dilate the aortic valve and deform the aortic valve flaps against the aorta wall adjacent the aortic valve. After the valvuloplasty step 520, delivery of the valve stent 505 is initiated by stabilizing the guidewire shaft (not shown) while the catheter body is withdrawn antegrade relative to the blood flow until the proximal anchor flange section of the valve stent 505 is exposed by the withdrawal of the capture sheath 503. The distal anchor flange of the valve stent 505 is then positioned at the junction between the aortic valve and the left ventricle at step 540, such that the distal anchor flange engages the ventricular surface of the aortic valve. The valve stent is fully deployed at step 550 by retrograde withdrawal of the catheter body 501 which continues to uncover the intermediate annular section of the valve stent and release the aortic valve stent 505 at the aortic valve site 510. In step 560, the valve stent 505 is completely deployed from the catheter 501 and the capture sheath 503. The distal anchor section of the valve stent 505 expands and contacts the lumenal wall of the aorta, immediately distal the aortic valve, thereby excluding the aortic valve flaps from the lumen of the prosthetic aortic valve stent 505. In step 570, the atraumatic tip and guidewire are retracted by retrograde movement of the guidewire shaft of the catheter, and the catheter 501 is withdrawn from the patient. FIGS. 20H and 20I depict the implanted valve stent 505 during diastole and systole, respectively. During ventricular diastole 580, the left ventricle expands to draw blood flow 506 from the left atrium into the left ventricle. A resultant negative pressure gradient is exerted across the valve stent 505, and the valve arms and valve flaps 506 of the valve stent 505 are biased to the closed position to prevent a regurgitation flow 507 from passing through the valve stent 505 and into the left ventricle 504. During ventricular systole 590, the left ventricle contracts and exerts a positive pressure across the valve stent 505, which overcomes the bias of the valve arms and valve flaps, which open 508 against the lumenal wall of the intermediate annular section of the valve stent and permit the ejection fraction 509 to be ejected from the left ventricle and into the aorta.

The method for delivery of the CC valve stent 40 or the VV valve stent 50 is identical to that of the CV stent 10 depicted in FIGS. 20A-20I, except that the anatomical location where delivery and deployment of the valve stent occurs is, of course, different.

Thus, while the present invention, including the different embodiments of the valve stent, the delivery and deployment method and the single catheter valvuloplasty and delivery system, have been described with reference to their preferred embodiments, those of ordinary skill in the art will understand and appreciate that the present invention is limited in scope only by the claims appended hereto.

What is claimed is:

1. An implantable valvular prosthesis, comprising:
    a. a stent body member having luminal and abluminal surfaces thereof and a central opening along a central longitudinal axis of the stent body member;
    b. a graft member comprising an outer graft member coupled to the abluminal surface of the stent body member and an inner graft member coupled to the luminal surface of the stent body member, wherein a terminal portion of the inner graft member is everted inwardly toward the central longitudinal axis of the stent body member;
    c. at least one biasing arm coupled to and projecting from the stent body member and into the central opening of the stent body member;
    d. at least one valve flap member formed by the terminal portion of the inner graft member coupled to the at least one biasing arm, the at least one valve flap member assuming a position, under zero pressure differential across the prosthesis, which occludes the central opening of the stent body member.

2. The implantable valvular prosthesis according to claim 1, wherein the stent body member further comprises a proximal anchoring section.

3. The implantable valvular prosthesis according to claim 2, wherein the stent body further comprises a distal anchoring section.

4. The implantable valvular prosthesis according to claim 2, wherein the proximal anchoring section further comprises a plurality of stent struts which project radially outward away from the central longitudinal axis of the stent body member.

5. The implantable valvular prosthesis according to claim 1, wherein the stent body member further comprises a distal anchoring section.

6. The implantable valvular prosthesis according to claim 5, wherein the distal anchoring section further comprises a radially enlarged section of the stent body member which communicates with the central opening of the stent body member.

7. The implantable valvular prosthesis according to claim 1, wherein the at least one valve flap member comprises a plurality of valve flap members, each of the plurality of valve flap members coupled at a terminal end portion thereof to a luminal surface of the inner graft member.

8. The implantable valvular prosthesis according to claim 7, wherein the plurality of valve flap members are coupled at equidistantly spaced intervals about the luminal surface of the inner graft member.

9. The implantable valvular prosthesis according to claim 1, further comprising:
 a. a catheter body defining a central longitudinal lumen, the catheter body comprises a distal stent capturing section capturing the stent body member;
 b. a guidewire shaft positioned co-axially within the central longitudinal lumen of the catheter body and passing through an entire longitudinal length of the catheter body; and
 c. an annular plug member concentrically coupled to the guidewire shaft and positioned proximal the distal stent capturing section, the annular plug member terminating the central longitudinal lumen of the catheter body in a fluid tight manner and being moveable within the distal stent capturing section.

10. A method of manufacturing an implantable valvular prosthesis, comprising the steps of:
 Fashioning a generally tubular stent body member, having a luminal and an abluminal surface and a central opening along a central longitudinal axis;
 Fashioning a graft;
 Attaching the graft to at least portions of both the luminal and abluminal surfaces of the stent body member, wherein the attachment of the graft to the stent body member forms at least one valve flap by everting a terminal portion of the graft inwardly toward the central longitudinal axis of the stent body member; and
 Wherein the step of fashioning the generally tubular stent body member further comprises shaping the stent body member to include at least one valve arm or blood flow regulator strut coupled to and projecting from the stent body member.

11. The method of claim 10, wherein the step of fashioning the generally tubular stent body member further comprises shaping the stent body member to include proximal and distal anchors.

12. The method of claim 11, wherein the proximal and distal anchors are present at opposing ends of the prosthesis.

13. The method of claim 10, wherein the step of fashioning the generally tubular stent body member further comprises shaping the stent body member to include an intermediate stent section.

\* \* \* \* \*